United States Patent [19]

Gut

[11] Patent Number: 4,751,501

[45] Date of Patent: Jun. 14, 1988

[54] VARIABLE AIR VOLUME CLOGGED FILTER DETECTOR

[75] Inventor: Edward B. Gut, Cook, Ill.

[73] Assignee: Honeywell Inc., Minneapolis, Minn.

[21] Appl. No.: 308,951

[22] Filed: Oct. 6, 1981

[51] Int. Cl.⁴ .......................................... G01N 15/08
[52] U.S. Cl. ...................................... 340/607; 55/274; 73/38
[58] Field of Search ............... 340/607, 608, 611, 626; 137/557; 55/274; 364/510; 73/38

[56] References Cited

U.S. PATENT DOCUMENTS

| | | |
|---|---|---|
| 3,263,403 | 8/1966 | Ladusaw .................................. 55/274 |
| 3,412,786 | 11/1968 | Taylor ..................................... 73/38 |
| 3,936,284 | 2/1976 | Mason ..................................... 55/274 |
| 3,939,457 | 2/1976 | Nelson .................................. 340/607 |
| 4,033,733 | 7/1977 | Nelson ..................................... 55/274 |
| 4,050,291 | 9/1977 | Nelson ..................................... 55/274 |
| 4,249,164 | 2/1981 | Tivy ..................................... 340/611 |
| 4,311,037 | 1/1982 | Gotchel .................................... 73/38 |

Primary Examiner—Gerald L. Brigance
Attorney, Agent, or Firm—Donald J. Lenkszus

[57] ABSTRACT

A system for detecting a clogged filter in a variable air volume system having a differential pressure sensor for sensing the differential pressure drop across the filter, an air flow sensor for sensing the air flow through the duct in which the filter is located, and a difference sensor connected to the differential pressure sensor and the air flow sensor to indicate when the filter is clogged.

3 Claims, 1 Drawing Sheet

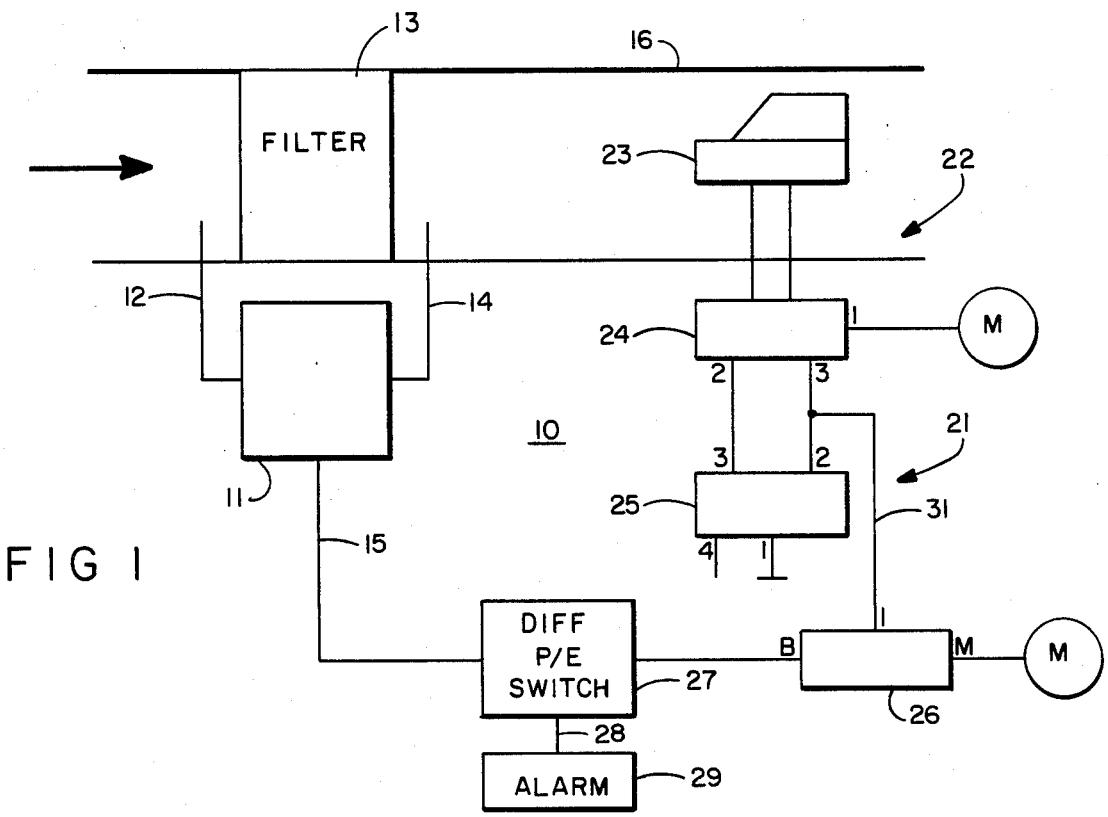
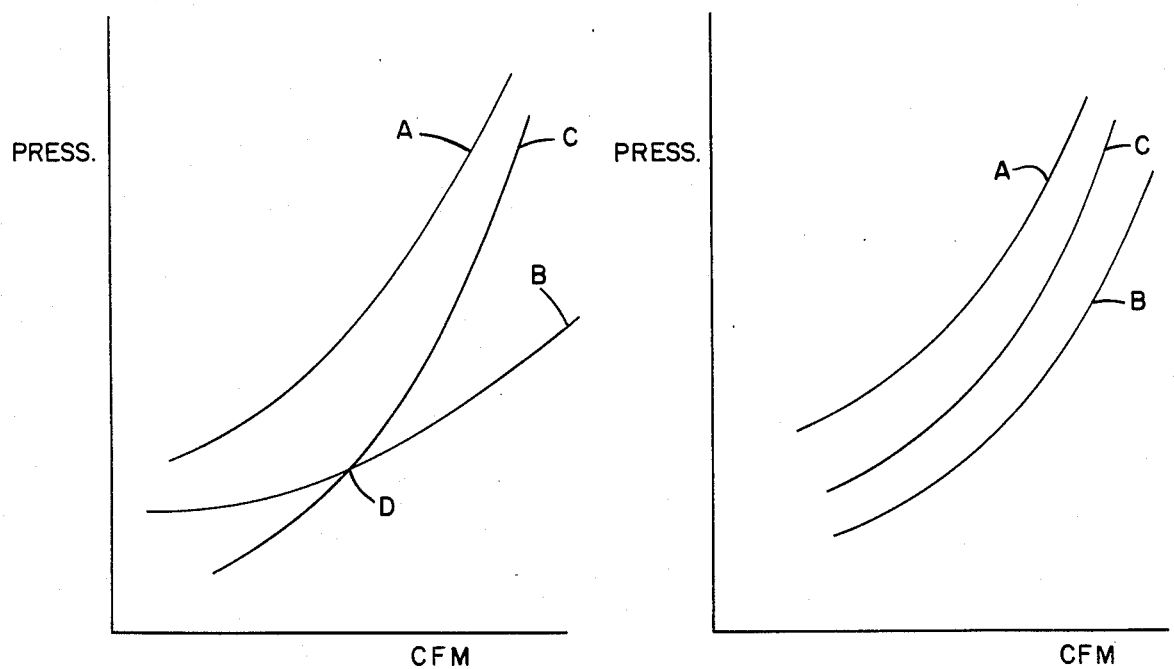
FIG 1
FIG 2
FIG 3

VARIABLE AIR VOLUME CLOGGED FILTER DETECTOR

BACKGROUND OF THE INVENTION

The present invention relates to a system for detecting clogged filters in variable air volume air conditioning sytems.

Any building whether residential or commercial having forced air systems for heating and cooling the interior of the building has a requirement for a filter to take out of the air being delivered to the interior of the building any dirt or airborne foreign particles. Either the filters are commercially available fiber glass filters which require periodic replacement or electrostatic air cleaners which require periodic cleaning. In order to replace or clean the air filter when it is dirty, the owner or maintenance personnel of the building must rely upon either their own memories or some sort of an automatic follow up system in order to avoid waiting too long for the replacement or cleaning of the air filter. Dirty air filters, as is well known, impede the air movement of the heated or cooled air throughout the building thus raising the energy costs of maintaining the desired temperature within the building.

There have been automatic systems for detecting clogged air filters which typically involve sensing the pressure drop across the air filter. As the air filter becomes dirty, the static pressure across the air filter begins to increase for any given air velocity moving through the duct in which the air filter is located. Simply using the pressure drop across the air filter in this type of air conditioning system is sufficient to determine whether or not there is a clogged filter for constant volume systems.

In variable air volume systems, however, the pressure drop across an air filter will vary according to the air volume moving through the duct in which the air filter is located in response to varying air flows. Thus, the detection of a change in the pressure drop across an air filter does not necessarily mean that the air filter has become clogged but may mean that the velocity of air moving through the duct has changed.

SUMMARY OF THE INVENTION

In order to detect clogged filters in variable air volume systems, the present invention provides a system for detecting a clogged filter having a pressure drop detection circuit for detecting the pressure drop across the filter, an air flow detection sensor for sensing air flow through the duct, and a comparison circuit which is connected to the pressure drop detector and the air flow detector sensor for providing an appropriate output indicating that the filter is clogged. The air flow detector then becomes a form of reference against which the pressure drop across the filter is compared. Thus, as the pressure drop across the filter changes because of changes in air velocity, the reference will change from the air flow detector because the air flow was also changing. Therefore, indications of a clogged filter will not be given merely because air flow within the duct has changed.

BRIEF DESCRIPTION OF THE DRAWINGS

These and other features and advantages will become apparent from a detailed description of the invention when taken in conjunction with the drawings in which:

FIG. 1 shows the clogged filter detecting system according to the present invention;

FIG. 2 shows the pressure curves for the system of FIG. 1; and,

FIG. 3 shows the modified pressure curves for the system of FIG. 1.

DETAILED DESCRIPTION

System 10 for detecting a clogged filter includes differential pressure sensor 11 which may be in the form of a Honeywell PP904B comprising static pressure tube 12 on the upstream side of filter 13 and static pressure tube 14 on the downstream side of filter 13. Sensor 11 provides in its output line 15 a pneumatic signal or pressure which is proportional or dependent upon the difference in pressure as sensed by tubes 12 and 14.

It will be noted that, as the filter becomes clogged because of dirt and airborne foreign particles, the differential pressure across filter 13 increases. If filter 13 is relatively clean, the static pressure drop across it is relatively small and increases as filter 13 becomes clogged or dirty. If filter 13 is totally clogged, its differential pressure thereacross will be at a maximum.

It should also be noted that the velocity of the air flowing through duct 16 will affect the pressure drop across filter 13. The pressure drop is less for lower air velocities and greater for higher air velocites. Since it might be possible for the output pressure from differential pressure sensor 11 in line 15 to exceed the limit, which limit would ordinarily indicate an unsatisfactorily clogged filter, due primarily to an increase in the air velocity or the air moving through duct 16, an air flow sensing means 21 has been included to provide a reference, which is dependent upon the velocity of air moving through duct 16, against which the output from differential pressure sensor 11 can be compared.

Thus, air flow sensing means 21 comprises a velocity sensor such as velocity sensor 22 which may be a Honeywell Velocitrol CP980B. Velocity sensor 22 is comprised of sensing head 23 and controller 24. Sensing head 23 comprises a primary nozzle supplied with main pressure and a secondary nozzle aligned opposite to the primary nozzle and transversely to the air flowing through duct 16. Thus, the primary nozzle issues a jet of air toward the secondary nozzle. The amount of air from the primary nozzle which is received by the secondary nozzle is dependent upon the velocity of the air moving through duct 16. As the air velocity increases, the amount of air received by the secondary nozzle decreases and as the velocity of air decreases the amount of air received by the secondary nozzle increases.

Controller 24 is connected to a reversing relay 25 which may be in the form of a Honeywell RP972A. Port 1 of this reversing relay is capped whereas in normal operaton it is connected to main pressure. Port 4 is connected to atmosphere and ports 2 and 3 are connected to the controller as shown. Since the Velocitrol is a controller, it has a narrow range of operation. Reversing relay 25 is connected as shown in order to increase the range of velocity sensor 22.

The output from velocity sensor 22 is connected to a characterizing relay 26 which forms a further element of air flow sensing means 21. Characterizing means 26 may be in the form of a Honeywell RP908. Depending upon the type of filter 13 used in the air conditioning system to which this invention can be applied, it can happen that the curve representing the pressure in line 31 versus duct air flow in cubic feet per meter (CFM) can cross the clean filter curve, i.e. the pressure in line 15 versus air flow. Thus, if the pressure in line 31 is below the clean filter signal in line 15, system 10 may provide a indication of a dirty filter when the filter is not dirty. Thus, characterizing means 26 can be arranged to insure that over substantially the entire range of response of air flow sensor 22, the curve of the pressure in line 31 will remain above the curve of the pressure in line 15 when filter 13 is clean.

In other words, as shown in FIG. 2, curve A represents the curve of a dirty filter in terms of the pressure in line 15 as a function of air flow in duct 16, curve B represents the curve of a clean filter, and curve C represents the pressure in line 31 as a function of air flow. As can be seen, if air flow is below point D where curves B and C intersect, an alarm may be given. Therefore, the characterizing means 26 characterizes curve C to take the form as shown in FIG. 3. Thus, when filter 13 becomes clogged beyond a desirable level, the pressure in line 15 will exceed the pressure in line 17 over substantially the entire range of both curves A and C.

The output of characterizing means 26 is connected to one input of difference sensing device 27 and the output from differential pressure sensor 11 is connected to the other input of difference sensing device 27. Difference sensing device 27 can be a pneumatic-to-electric switch which will provide a change in its electrical output over line 28 when the pressure in line 15 exceeds the pressure in line 27.

It can be seen that, although changes in the velocity of air moving through duct 16 will move curves A and B up and down the pressure scale, reference curve C provided by air flow sensing means 21 will similarly move so that curve C will always remain just below the output from differential pressure sensor 11 when filter 13 has not reached the predetermined clogged level at which an alarm or signal is given. When filter 13 becomes clogged beyond the predetermined limit, the pressure in line 15 will exceed the pressure in line 27 as curve A exceeds curve C and an output on electrical line 28 will energize alarm 29 to give an indication of the clogged filter.

The embodiments of the invention in which an exclusive property or right is claimed are defined as follows:

1. A system for detecting a clogged filter in a variable air volume air conditioning duct system comprising:
   first means for detecting the pressure drop across said filter and comprising a differential pressure sensor for providing a differential pressure output dependent upon the pressure drop across said filter;
   velocity sensor means having a velocity sensing head arranged to be mounted within said duct for providing an air flow output pressure indicative of the velocity of air moving through a duct in which said filter is located; and,
   means connected to said first and second means for providing an output signal indicating when said filter is clogged and comprising, said velocity sensor means comprises sensor for providing an output signal indicative of the velocity of air moving through said duct and characterizing means connected to receive said output signal for characterizing said air flow output pressure so that said air flow output pressure remains below a predetermined clean filter level over a substantial portion of its range; and,
   a difference sensing pneumatic-to-electric switch which will provide a switched output when said differential pressure output from said differential pressure sensor exceeds said air flow output pressure from said characterizing means.

2. A system for detecting a clogged filter in a variable air volume air conditioning duct system comprising:
   first means for detecting the pressure drop across said filter
   velocity sensor means having velocity sensing head arranged to be mounted within said duct for providing an air flow output pressure indicative of the velocity of air moving through a duct in which said filter is located said velocity sensor means comprises a velocity sensor for providing an air flow output signal indicative of the velocity of air moving through said duct and characterizing means connected to receive said output signal for characterizing said air flow output pressure so that said air flow output pressure remains below a predetermined clean filter level over a substantial portion of its range; and
   means connected to said first and second means for providing an output signal indicating when said filter is clogged and comprising a difference sensing pneumatic-to-electric switch will provide a switched output when an output pressure from said first means exceeds said air flow output pressure from said characterizing means.

3. A system for detecting a clogged filter in a variable air volume air conditioning duct system comprising:
   first means for detecting the pressure drop across said filter;
   velocity sensor means having a velocity sensing head arranged to be mounted within said duct for providing an air flow output pressure indicative of the velocity of air moving through a duct in which said filter is located; and,
   means connected to said first and second means for providing an output signal indicating when said filter is located; and
   means connected to first and second means for providing an output signal indicating when said filter is clogged and comprising a difference sensing pneumatic-to-electric switch will provide a switched output when an output pressure from said first means exceeds an output pressure from said second means.

* * * * *